United States Patent
Nokihara et al.

(10) Patent No.: US 12,103,983 B2
(45) Date of Patent: Oct. 1, 2024

(54) COMPOUND AND ANGIOGENIC AGENT COMPRISING SAME

(71) Applicant: HiPep Laboratories, Kyoto (JP)

(72) Inventors: Kiyoshi Nokihara, Kyoto (JP); Yuki Tominaga, Kyoto (JP); Atsushi Kitagawa, Kyoto (JP); Shun Nokihara, Kyoto (JP)

(73) Assignee: HIPEP LABORATORIES, Kyoto (JP)

( * ) Notice: Subject to any disclaimer, the term of this patent is extended or adjusted under 35 U.S.C. 154(b) by 709 days.

(21) Appl. No.: 17/299,035

(22) PCT Filed: Oct. 31, 2019

(86) PCT No.: PCT/JP2019/042953
§ 371 (c)(1),
(2) Date: Jun. 2, 2021

(87) PCT Pub. No.: WO2020/116062
PCT Pub. Date: Jun. 11, 2020

(65) Prior Publication Data
US 2022/0041656 A1  Feb. 10, 2022

(30) Foreign Application Priority Data
Dec. 3, 2018 (JP) .................................. 2018-226244

(51) Int. Cl.
*C07K 7/06* (2006.01)
*A61K 38/00* (2006.01)
*C07K 7/64* (2006.01)

(52) U.S. Cl.
CPC .................. *C07K 7/06* (2013.01); *C07K 7/64* (2013.01); *A61K 38/00* (2013.01)

(58) Field of Classification Search
None
See application file for complete search history.

(56) References Cited

FOREIGN PATENT DOCUMENTS

| EP | 1 452 182 A1 | 9/2004 |
| JP | 4338516 A | 7/2009 |
| WO | WO 2005/094865 A1 | 10/2005 |
| WO | WO2005/095443 A1 | 10/2005 |

OTHER PUBLICATIONS

Hamada et al., "Angiogenic activity of osteopontin-derived peptide SVVYGLR," Biochemical and Biophysical Research Communications (2003), vol. 310, pp. 153-157.
International Search Report mailed Feb. 4, 2020, in PCT/JP2019/042953.
Chen et al., "Pharmacokinetics and tumor retention of 125I-labeled RGD peptide are improved by PEGylation", Nuclear Medicine and Biology, vol. 31, No. 1, Jan. 1, 2004, pp. 11-19.
Extended European Search Report for European Application No. 19891727.0, dated Dec. 9, 2022.
Tominaga et al., "Improved design of peptides exhibiting angiogenic activities for clinical applications" Bioorganic & Medicinal Chemistry, vol. 28, No. 19, Oct. 1, 2020, pp. 1-4.

*Primary Examiner* — Sergio Coffa
(74) *Attorney, Agent, or Firm* — Birch, Stewart, Kolasch & Birch, LLP

(57) ABSTRACT

Disclosed are a novel compound having a higher angiogenic effect than that of a known peptide-based angiogenic agent, and an angiogenic agent including the novel compound. The compound is represented by the following formula [1]: Cyclic(Cys-O2Oc-SVV(F/Y)GLRG-Cys)-$NH_2$ (wherein the number of oxyethylene units, represented by O2Oc, is within the range of 2 to 6), the following formula [II]: Cyclic($O_2$Oc-SVV(F/Y)GLRQ)-$NH_2$ [II] (wherein the number of oxyethylene units, represented by O2Oc, is within the range of 2 to 6), or the following formula [III]: $O_2$Oc-SVV(F/Y)GLR-$NH_2$ [III] (wherein the number of oxyethylene units, represented by O2Oc, is within the range of 2 to 6).

12 Claims, 6 Drawing Sheets
Specification includes a Sequence Listing.

COMPOUND AND ANGIOGENIC AGENT COMPRISING SAME

TECHNICAL FIELD

The present invention relates to a novel compound, and an angiogenic agent comprising the same. The angiogenic agent of the present invention is useful not only for treatment of ischemic diseases, but also for regeneration, repair, and transplantation of organs using biological substitute materials such as artificial bones.

BACKGROUND ART

Ischemic diseases due to vascular occlusion, such as myocardial infarction and cerebral infarction, account for a considerable fraction of causes of death in Japan at present. Even in cases where the ischemic diseases do not cause death, some of them, including obstructive aortic sclerosis, may lead to deterioration of QOL (quality of life) when amputation of lower limbs is required. For these ischemic diseases, angiogenesis therapy based on formation of new blood vessels has been expected to be useful. Conventionally, apatite, titanium, and the like have been used as bone-filling materials and implant materials. These conventional biomaterials often fail to sufficiently produce their original functions because of their poor compatibilities with the surrounding soft and hard tissues. Angiogenesis plays important roles also in engraftment of biomaterials in, for example, regeneration and repair of organs using biological substitute materials such as artificial bones. In regenerative medicine, organ substitutes, biomaterials, and the like are implanted. Their engraftment at the implantation sites indispensably requires angiogenesis for transportation of oxygen and nutrients, and QOL after the implantation is said to be dependent on rapid adhesion and angiogenesis.

For achieving better compatibility with the surrounding soft and hard tissues, use of bioadhesive functional molecular peptides has been proposed. For example, use of a composite prepared by mixing a carbonate apatite whose composition and crystallinity are similar to those of hard tissues in the body, with collagen, which is a bioadhesive functional molecular peptide, as a bone substitute has been proposed (K. Nokihara et al., The Japanese Peptide Society, Osaka, 373-376, 2001, Development of Biomimetic Materials: Novel Composite Material Carrying Immobilized Functional Peptides; M. Okazaki et al., Dentistry in Japan, 37, 95-100, 2001, A New Concept of C03 apatite-Collagen Composites with Adhesion Motif as Biomaterials). This composite has good biocompatibility, and is promising as a biomimetic bone substitute.

Once blood vessels are newly formed on the surfaces and insides of such biomaterials, abundant blood allows sufficient supply of nutrients and oxygen to the cells on the surfaces and insides of the implanted biomaterials at an early stage after the operation, to allow formation of optimal environment for the cells to function, resulting in favorable engraftment in the body, which is advantageous.

In recent years, studies have been intensively carried out for regenerative medicine which enables avoidance of rejection, by means of transplantation of cells derived from an autologous tissue by the technique of induced pluripotent stem cells (iPS). For example, studies are being carried out based on the idea that curative treatment of diabetes, for which only symptomatic treatment is available at present, may be possible by transplantation of autologous cells using iPS (transplantation of pancreatic islet beta cells). A key factor for engraftment of the cells is generation of blood vessels at the transplantation site.

In regenerative medicine, it has been conventionally well known that nerve growth factor (NGF) and basic fibroblast growth factor (bFGF) are effective to some extent. However, they are known to cause malignant transformation or infiltration, and this is practically problematic in clinical application.

On the other hand, the present inventors have previously invented an angiogenic agent composed of a peptide, and it has been patented (Patent Document 1). Since peptides are metabolized and degraded into amino acids in the body, they are highly advantageous from the viewpoint of safety. Needless to say, it would be advantageous if an angiogenic agent having a higher angiogenic effect in the body than that of the known peptide-based angiogenic agent described in Patent Document 1 is obtained.

PRIOR ART DOCUMENT

Patent Document

[Patent Document 1] JP 4338516 B

SUMMARY OF THE INVENTION

Problems to be Solved by the Invention

An object of the present invention is to provide a novel compound having a higher angiogenic effect than that of the peptide-based angiogenic agent described in Patent Document 1, and an angiogenic agent comprising the novel compound.

Means for Solving the Problems

AGP, which is the angiogenic agent described in Patent Document 1, is a low-molecular-weight peptide. Since it has no side effect, it is safe, but its effectiveness is only weakly persistent. As a result of a study on the cause, the weak persistence was thought to be due to a short half-life (due to degradation/metabolism in the body). In view of this, the present inventors paid attention to persistence of the effect, and improved the structure of the agent, to give the agent resistance to endogenous enzyme in the body. Although one possible solution may be utilization of non-natural amino acids, they could be toxic. The inventors therefore attempted designing of the agent by modification of the N- and C-termini such that the agent has resistance to endogenous enzyme in the body. Since AGP originally has an adhesive action, the agent can be expected to have compatibility with the tissues surrounding the implant.

From such a point of view, the present inventors intensively studied to discover a novel compound having a high angiogenic effect, thereby completing the present invention.

More specifically, the present invention provides the following.

(1) A compound represented by the following formula [I]:

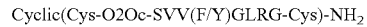

(wherein the number of oxyethylene units, represented by O2Oc, is within the range of 2 to 6), the following formula [II]:

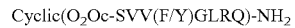    [II]

(wherein the number of oxyethylene units, represented by O2Oc, is within the range of 2 to 6),
or
the following formula [III]:

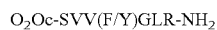   [III]

(wherein the number of oxyethylene units, represented by O2Oc, is within the range of 2 to 6).

(2) The compound according to (1), represented by the following formula [IV]:

   [IV]

(wherein the number of oxyethylene units, represented by O$_2$Oc, is within the range of 2 to 6).

(3) The compound according to (2), represented by the following formula [V]:

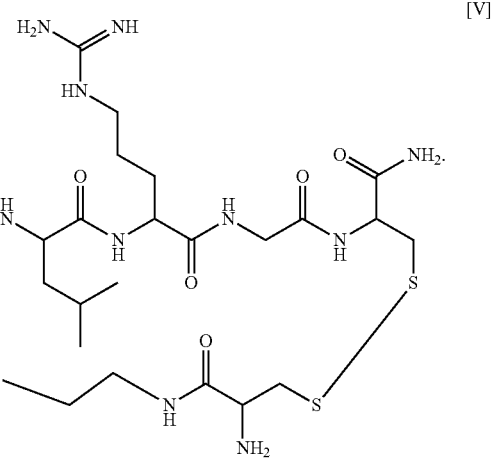

(4) The compound according to (3), wherein both of the two Cys's in the formula [V] are L-isomers.
(5) The compound according to (3), wherein both of the two Cys's in the formula [V] are D-isomers.
(6) The compound according to (1), represented by the following formula [VI]:

   [VI]

(wherein the number of oxyethylene units is within the range of 2 to 6).

(7) The compound according to (2), represented by the following formula [VII]:

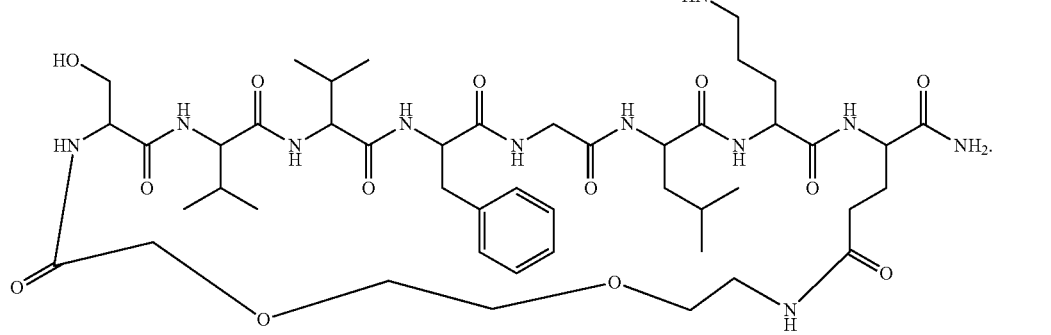

(8) The compound according to (1), represented by the following formula [VIII]:

O₂Oc-SVVFGLR-NH₂  [VIII]

(wherein the number of oxyethylene units, represented by O₂Oc, is within the range of 2 to 6).

(9) The compound according to (8), represented by the following formula [IX]:

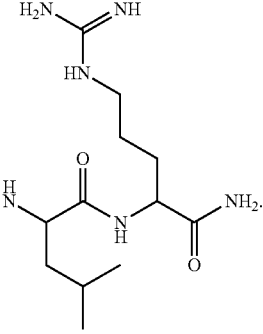

(10) An angiogenic agent comprising the compound according to any one of (1) to (9) as an active component.
(11) The compound according to any one of (1) to (9), for use as an angiogenic agent.
(12) Use of the compound according to any one of (1) to (9), for the production of an angiogenic agent.
(13) An angiogenesis method comprising administering an effective amount of the compound according to any one of (1) to (9) to a subject in need of angiogenesis.

Effect of the Invention

By the present invention, a novel compound having an excellent angiogenic action, and an angiogenic agent comprising it as an active component, were provided.

MODE FOR CARRYING OUT THE INVENTION

Figure 1:
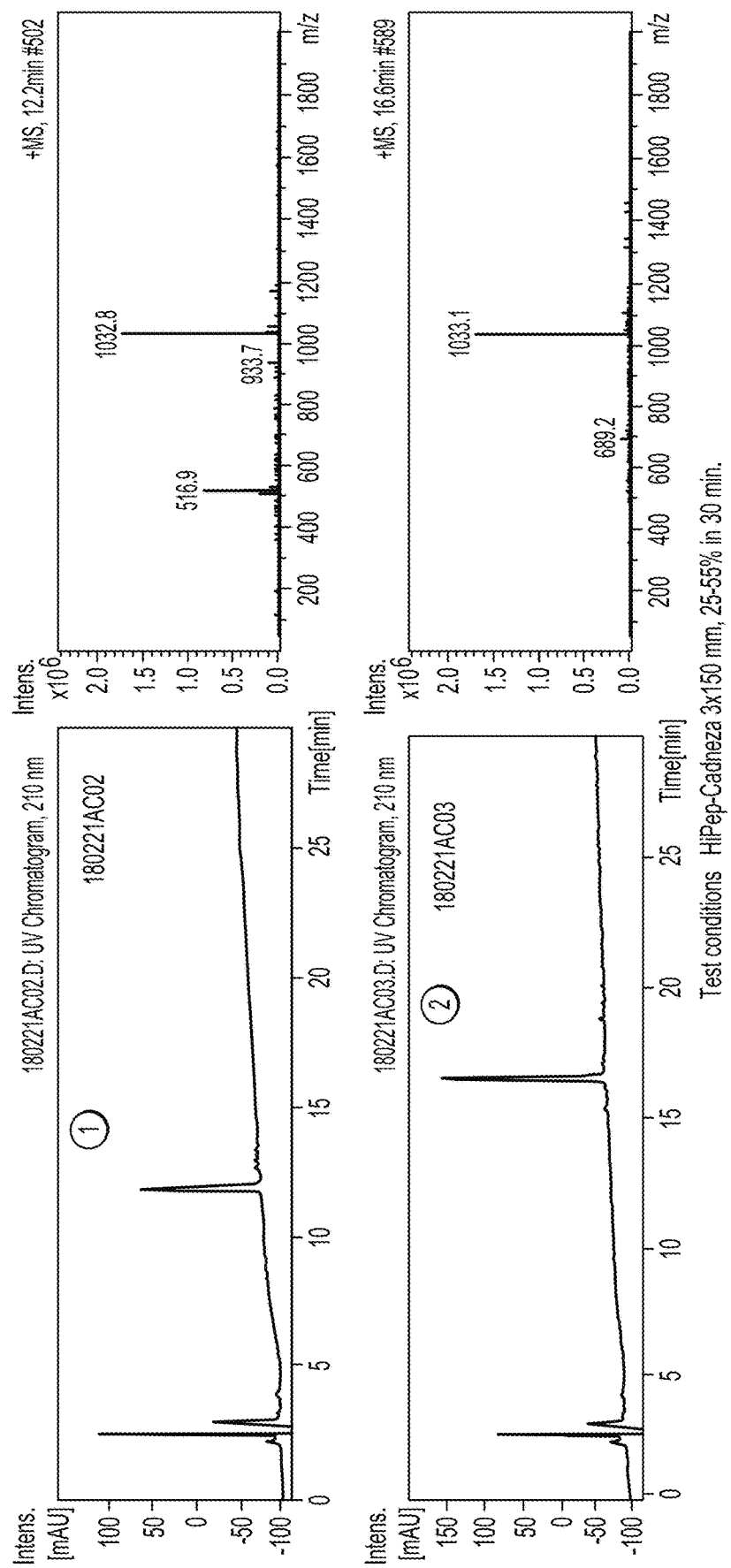
FIG. 1 is a diagram illustrating the results of HPLC and LCMS for the compound of Example 1.
Figure 2:
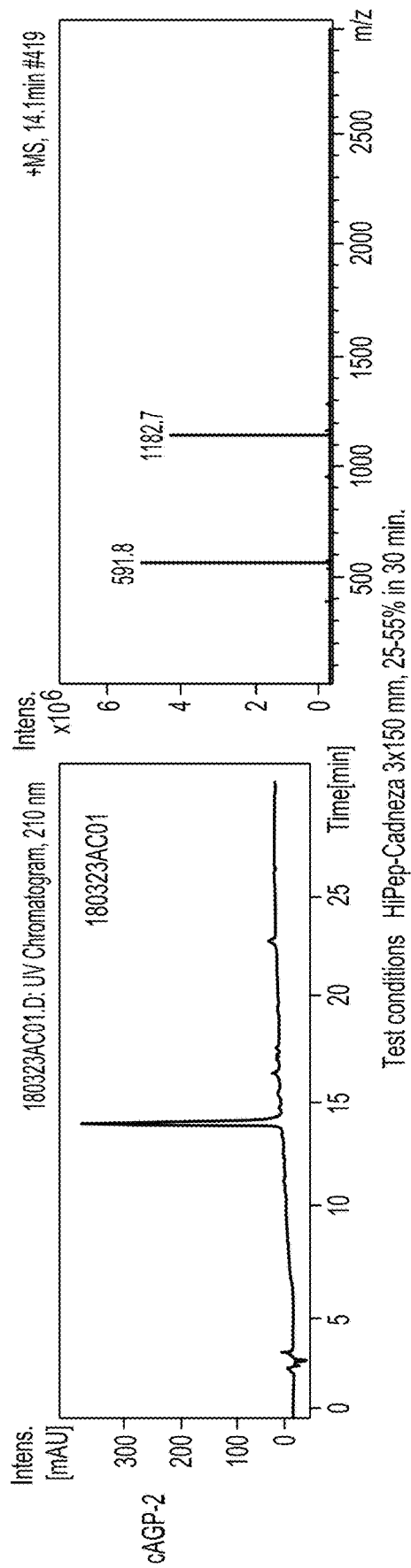
FIG. 2 is a diagram illustrating the results of HPLC and LCMS for the compound of Example 2.
Figure 3:
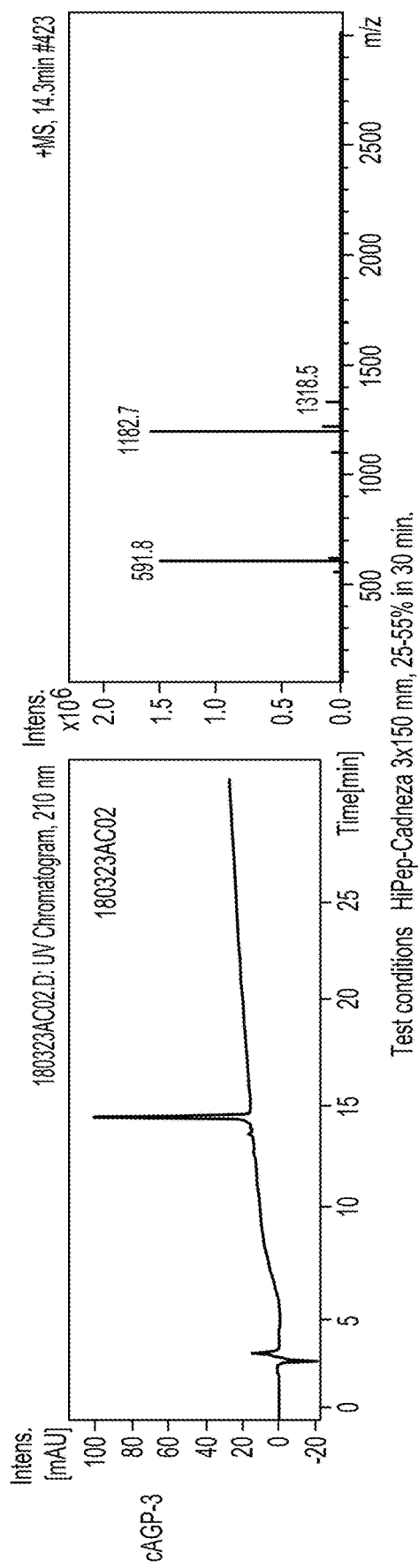
FIG. 3 is a diagram illustrating the results of HPLC and LCMS for the compound of Example 3.
Figure 4:
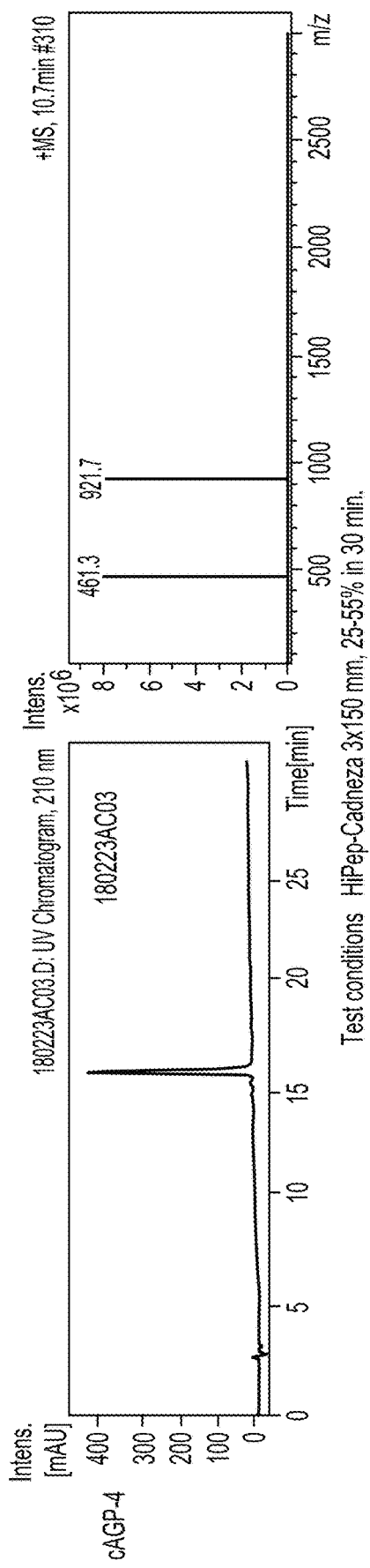
FIG. 4 is a diagram illustrating the results of HPLC and LCMS for the compound of Example 4.

As described above, the compound of the present invention is a compound represented by the following formula [I]:

Cyclic(Cys-O2Oc-SVV(F/Y)GLR-G-Cys)-NH₂

(wherein the number of oxyethylene units, represented by O2Oc, is within the range of 2 to 6), the following formula [II]:

Cyclic(O₂Oc-SVV(F/Y)GLRQ)-NH₂  [II]

(wherein the number of oxyethylene units, represented by O2Oc, is within the range of 2 to 6),
or
the following formula [III]:

O₂Oc-SVV(F/Y)GLR-NH₂  [III]

(wherein the number of oxyethylene units, represented by O2Oc, is within the range of 2 to 6).

In the formula [1], the portion "SVV(F/Y)GLRG" represents an amino acid sequence expressed in the single-letter code of amino acids, and "(F/Y)" at the fourth position from the N-terminus means phenylalanine or tyrosine. Thus, SVV(F/Y)GLRG represents SVVFGLRG (SEQ ID NO:1) or SVVYGLRG (SEQ ID NO:2). The sequence having phenylalanine as the fourth amino acid is more preferred since it has a higher angiogenic activity. Although each amino acid constituting these amino acid sequences may independently be either an L-isomer or a D-isomer, L-isomers are more advantageous since they have less concerns about side effects and the like, and since they are economically advantageous in industrial production.

The compound represented by the above-described formula [I] (having phenylalanine as the fourth amino acid) wherein the number of oxyethylene units (—O—CH₂—CH₂—) in the cross-linking moiety is two, is represented by the above-described structural formula [V].

Among the compounds represented by the above-described structural formula [V], those in which both of the two Cys's are L-isomers or in which both of the two Cys's are D-isomers are preferred. From an economic point of view, the compound in which both of the two Cys's are L-isomers is especially preferred.

In the above-described formula [II], the portion "SVV(F/Y)GLRQ" represents an amino acid sequence expressed in the single-letter code of amino acids, and "(F/Y)" at the fourth position from the N-terminus means phenylalanine or tyrosine. Thus, SVV(F/Y)GLRQ represents SVVFGLRQ (SEQ ID NO:3) or SVVYGLRQ (SEQ ID NO:4). The sequence having phenylalanine as the fourth amino acid is more preferred since it has a higher angiogenic activity. Although each amino acid constituting these amino acid sequences may independently be either an L-isomer or a D-isomer, L-isomers are more advantageous since they have less concerns about side effects and the like, and since they are economically advantageous in industrial production.

The compound represented by the above-described formula [II] (having phenylalanine as the fourth amino acid) wherein the number of oxyethylene units (—O—CH$_2$—CH$_2$—) in the cross-linking moiety is two, is represented by the following structural formula [VIII].

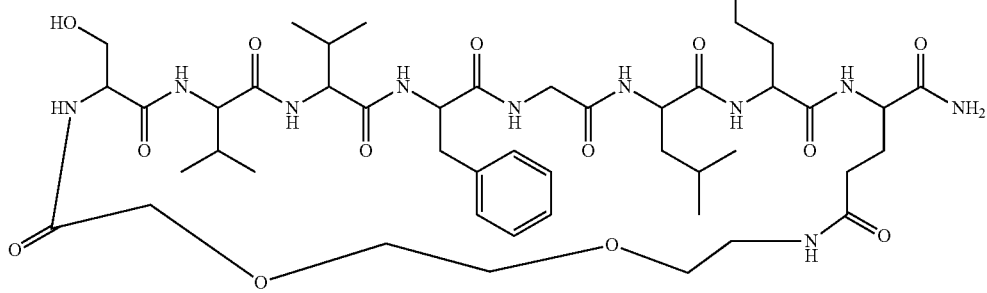

In this structure, the number of oxyethylene units in the cross-linking structure which is cross-linking both ends of the peptide may be 2 to 6, and the number is especially preferably two (as shown in the formula [VIII]). The compounds represented by the above-described formula [IV] include a plurality of kinds of stereoisomers. Any of the stereoisomers and mixtures thereof may also be used.

In the above-described formula [III], the portion "SVV(F/Y)GLR" represents an amino acid sequence expressed in the single-letter code of amino acids, and "(F/Y)" at the fourth position from the N-terminus means phenylalanine or tyrosine. Thus, SVV(F/Y)GLR represents SVVFGLR (SEQ ID NO:5) or SVVYGLR (SEQ ID NO:6). The sequence having phenylalanine as the fourth amino acid is more preferred since it has a higher angiogenic activity. Although each amino acid constituting these amino acid sequences may independently be either an L-isomer or a D-isomer, L-isomers are preferred since they have lower risks of side effects. Peptides having the amino acid sequence of SEQ ID NO:5 or SEQ ID NO:6 are described as angiogenic agents in Patent Document 1.

The compound represented by the above-described formula [III] (having phenylalanine as the fourth amino acid) wherein the number of oxyethylene units in the N-terminal additional moiety is two, is represented by the above-described structural formula [IX].

In each of the above compounds, the peptide moiety can be easily prepared by chemical synthesis using a commercially available peptide synthesizer. Methods of adding the O$_2$Oc structure to the N-terminus, and the cyclization, are concretely described in the Examples below, and the addition and the cyclization can be easily carried out also for compounds other than those in the Examples in accordance with the methods described in the Examples.

Each compound of the present invention described above (hereinafter referred to as "peptide-based compound" for convenience) may be topically administered alone or in the form of an injection solution in which the compound is dissolved in physiological buffer, to a tissue for which angiogenesis is desired. By topically administering the angiogenic agent of the present invention by a method such as injection, application, or spraying in the vicinity of a wound created by an operation or injury, angiogenesis is promoted, and hence curing of the wound is promoted. Here, the concentration of the peptide-based compound in the peptide-based compound solution used for the injection, or for the application or spraying, is not limited. The concentration is usually about 1 to 10 µg (micrograms)/mL. The dose may be appropriately selected depending on the size and depth of the wound or the like. The dose may be a dose with which the entire wound is covered with the peptide-based compound solution. One or several times of administration may be carried out every day or every several days until the wound is cured. The injection solution may also contain various other components usually contained in wound treatment agents, such as disinfectants and anti-inflammatory/analgesic agents.

The angiogenesis may be promoted by binding the peptide-based compound to a carrier, and embedding the carrier having the peptide-based compound bound thereto into the body. Such immobilization on the carrier allows the compound to selectively act on the desired site, and this system is promising as a new DDS (drug delivery system). By topically administering the angiogenic agent of the present invention by a method such as application or spraying at the site of implantation of the biomaterial, angiogenesis is promoted, and hence postoperative healing is promoted. Examples of the carrier include, but are not limited to, resins used for bone substitutes, tooth substitutes, artificial organs, and the like; and biopolymers such as proteins. By binding the peptide-based compound to a resin, and then embedding the resin into the body, angiogenesis in the surrounding tissue in contact with the resin is promoted, resulting in improvement of the affinity of the resin to the body. In a more preferred mode, a protein (the term "protein" herein includes protein-containing complexes such as glycoproteins and phosphoproteins unless otherwise specified) may be used as a carrier.

The protein used as the carrier herein may be any biocompatible protein, and is especially preferably a cell-adhesive protein from the viewpoint of better adhesion to the body tissue. Preferred examples of the cell-adhesive protein include, but are not limited to, collagen (gelatin), fibronectin, vitronectin, and laminin, and partial hydrolysates thereof. These proteins are preferably purified proteins prepared by removal of allergens, from the viewpoint of preventing allergic reactions. For example, various commercially available animal-derived collagens have low purity, contain allergens, and exhibit poor reproducibility of the quality. They are thus not preferred for clinical application. Gelatins prepared by partially hydrolyzing animal-derived collagen and removing allergens therefrom are commercially available for clinical application. Genetically produced human-type collagens are also commercially available. Such purified collagens and their hydrolysates are preferably used.

The amount of the peptide-based compound to be bound to the carrier is not limited, and may be appropriately selected. The weight ratio between the carrier and the peptide-based compound (carrier:peptide-based compound) is usually about 100:1 to 1:1, preferably about 20:1 to 5:1.

The binding between the carrier and the peptide-based compound is preferably achieved by covalent bonding. The binding can be easily carried out by, for example, binding the amino group at the N-terminus of the peptide-based compound to an arbitrary amino group in the carrier using a cross-linking agent such as glutaraldehyde, and an example of the binding method is described in detail in the Examples below. In cases of binding to a resin in an artificial organ or the like, the resin may be copolymerized with a monomer containing a group which can be used for binding to the peptide-based compound, such as an amino group, and this amino group or the like may be bound to the amino group at the N-terminus of the peptide-based compound.

The carrier having the peptide-based compound bound thereto may be applied or sprayed, or may be embedded as it is in the body. In cases where a cell-adhesive protein is employed as the carrier, the carrier having the peptide-based compound bound thereto may be used alone or together with other pharmacologically active components, as a suture thread, an orthopedic material, an adhesion-promoting agent for wounds, or the like. Further, the carrier protein having the peptide-based compound bound thereto may be mixed with carbonate apatite or other materials such as a cell-adhesive protein not having a peptide-based compound of the present invention bound thereto, and the resulting mixture may be used as a bone substitute or the like. In this case, the amount of the peptide-based compound contained in the final biomaterial such as a bone substitute is not limited, and usually about 0.1 mg to 10 mg per 100 g of the biomaterial.

The present invention is described below concretely based on Examples. However, the present invention is not limited to the following Examples.

1. Examples 1 to 4 and Comparative Example 1

The compounds shown below in Table 1 were synthesized. In the case of Comparative Example 1, water was added to provide a control. The two Cys's in the cAGP-2 in Example 2 are D-isomers. Except for these, all amino acids in all Examples are L-isomers.

TABLE 1

| Example | Compound code | Structure | Molecular weight |
|---|---|---|---|
| Example 1 | cAGP-1 | Cyclic amide Formula [VII] Cyclic(O2Oc-SVVFGLRQ)-NH$_2$ | 1032.19 |
| Example 2 | cAGP-2 | Disulfide Formula [V], wherein the two Cys's are D-isomers Cyclic(DCys-O2Oc-SVVFGLR-G-DCys)-NH$_2$ | 1182.42 |
| Example 3 | cAGP-3 | Disulfide Formula [V], wherein the two Cys's are L-isomers Cyclic(Cys-O2Oc-SVVFGLR-G-Cys)-NH$_2$ | 1182.42 |
| Example 4 | AGP-O2Oc | Linear Formula [IX] O2Oc-SVVFGLR-NH$_2$ | 921.10 |
| Comparative Example 1 | Control | H$_2$O, added as an angiogenesis control | 18.01 |

In the following description, a compound containing a peptide moiety, such as a cyclized peptide-based compound, may also be referred to as "peptide" for convenience.

1. Peptide Synthesis
Common Portion (Extension of Peptide Chain)

Peptide resins (designated cAGP (abbreviation of cyclic angiogenic peptide)) having the amino acid sequences shown in Table 1 were synthesized using an automated peptide synthesizer according to a high efficiency solid-phase method based on Fmoc chemistry (K. Nokihara et. al., Innovation and Perspectives in Solid-Phase Synthesis 1992, ed., R. Epton, Intercept Limited, Andover, UK, 445-448, 1992, Design and Applications of a Novel Simultaneous Multiple Solid-Phase Peptide Synthesizer; Kiyoshi Nokihara, Journal of Synthetic Organic Chemistry, Japan, 52, 347-358, 1994, Highly Efficient Peptide Synthesis: Automated Simultaneous Multiple Solid-Phase Synthesis and Peptide Library). Regarding the Gln residue in cAGP-1, extension during the synthesis is carried out using Fmoc-Glu(OAll)-OH, and it is converted to Gln during the cyclization.

cAGP-1 (All-Deprotection, Cyclization Reaction, Cleavage)

The peptide resin was washed with dichloromethane. Thereafter, 0.1 eq. of tetrakis(triphenylphosphine)palladium (0) was added thereto, and then 5 eq. of phenylsilane was added thereto, followed by shaking the resulting mixture (30° C., 2.5 hours). After washing with DMF (dimethylformamide), cyclization reaction (HATU 5 eq./DIEA (N,N-diisopropylethylamine, in DMF) 10 eq.; 30° C., 3.5 hours) was carried out. The peptide obtained by cleavage from the resin was assayed using a high-performance liquid chromatography mass spectrometer (HPLC-MS). As a result, the peptide was confirmed to be a desired product (consistent with the theoretical mass value). The peptide was purified by high-performance liquid chromatography (HPLC), and then freeze-dried to obtain the desired product. Since, in this process, two peaks with the same mass number were obtained at different elution positions (the lower panels in FIG. 1), these were separated and collected. By assaying the obtained peptides by LCMS, it was confirmed that one of them corresponds to the compound of Example 1 in the present invention (the upper panels in FIG. 1), that the other corresponds to a cyclic dimer thereof (which is outside the scope of the present invention), and that each of these is highly pure (a single component, consistent with the theoretical mass value).

cAGP-2, cAGP-3 (Cleavage, Cyclization)

Each peptide obtained by cleavage from the resin was assayed by HPLC-MS. As a result, the peptide was confirmed to be a desired product in the linear form (consistent with the theoretical mass value). The peptide was purified by HPLC, and then freeze-dried. The peptide obtained was dissolved in 0.1 M ammonium acetate, and dimethyl sulfoxide (DMSO) was added thereto to a concentration of 20% by weight, followed by shaking the resulting mixture overnight (final peptide concentration, 0.5 mg/mL). The mixture was diluted two-fold by addition of $H_2O$, and then freeze-dried. The crude peptide obtained was purified by HPLC, and then freeze-dried. The obtained peptide was assayed by LCMS, to confirm that it is highly pure (a single component, consistent with the theoretical mass value).

AGP-O2Oc (Cleavage)

The peptide obtained by cleavage from the resin was assayed by LCMS. As a result, the peptide was confirmed to be a desired product (consistent with the theoretical mass value). The peptide was purified by HPLC, and then freeze-dried. The obtained peptide was then assayed by LCMS, to confirm that it is highly pure (a single component, consistent with the theoretical mass value).

Common Process (Counter Ion Exchange)

Each of the highly pure peptides obtained by the above-described peptide synthesis and purification was redissolved in 0.01 N HCl/MeCN, and then freeze-dried, to convert it to hydrochloric acid salt.

The results of HPLC and LCMS for each compound obtained by the above method are shown in FIG. 1 to FIG. 4.

Example 3 Angiogenesis Assay

1. Method

Figure 5:
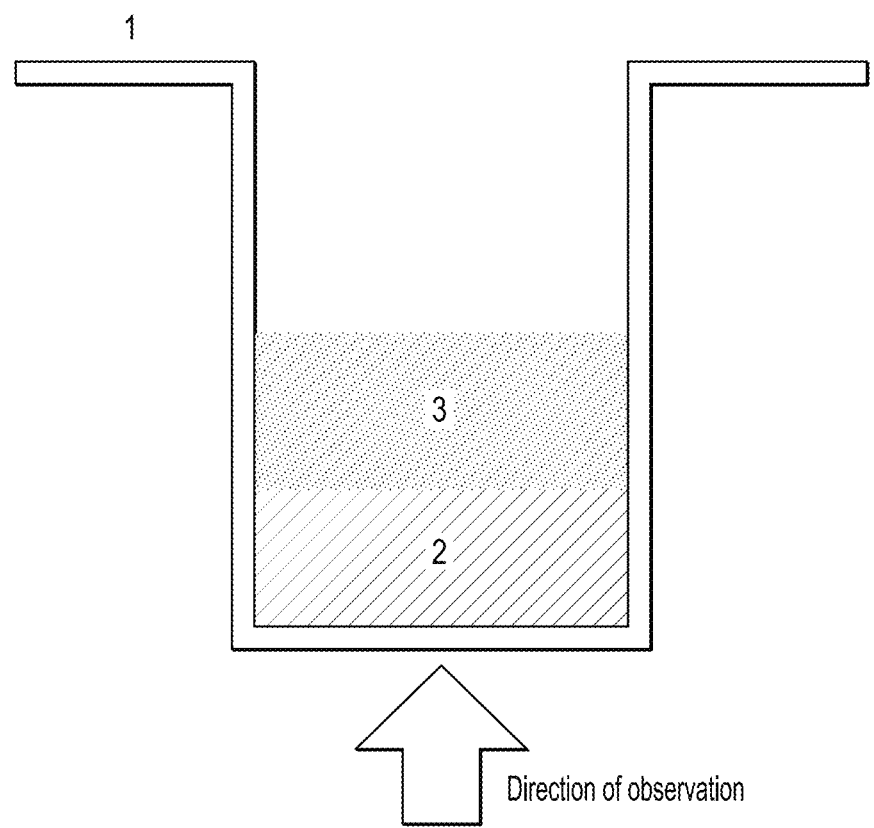
FIG. 5 is a diagram illustrating the method of the angiogenesis assay which was carried out in the Examples below.

In this assay, human umbilical vein endothelial cells (HUVEC, manufactured by Promocell GmbH) were used. Cell culture was carried out according to a method recommended by Promocell (vascular endothelial cells, manufactured by Promocell GmbH). More specifically, 25 mL of a vascular endothelial cell growth medium (manufactured by Promocell GmbH) was prepared in a culture flask, and P/S (100 mU/mL penicillin, 100 μg/mL streptomycin) was added thereto, followed by mixing the resulting mixture. Thereafter, 1 mL of a HUVEC cell suspension that had been frozen was added thereto, and the resulting mixture was lightly mixed, followed by starting culture at 37° C. An angiogenesis assay was carried out based on the method for the Angiogenesis assay kit (manufactured by Promocell GmbH). Since the cultured cells adhered to the bottom surface of the flask, the cells were detached and collected using a trypsin-EDTA solution, and the cell number was counted, followed by resuspending the cells in 1 mL of the medium ($1.74 \times 10^6$ cells). FIG. 5 shows a schematic diagram of the angiogenesis assay. In the figure, 1 represents a well of the 96-well microplate used in the assay. To each well, 50 μL of an extracellular matrix gel (included in the kit) was dispensed, and then the plate was incubated at 37° C. for 1 h to allow formation of the gel indicated by reference numeral 2. A mixture of a HUVEC cell suspension and each angiogenic factor (Table 1) was layered (reference numeral 3 in the figure) on the gel such that each well contained 17,400 cells and the angiogenic factor at a concentration of 1 μg/mL, and culture was performed at 37° C. in 5% $CO_2$ for 2 to 96 hours. During the culture, observation was carried out using an incident-light microscope from the direction of the arrow in the figure, for monitoring of angiogenesis.

2. Results

In the early stage of the culture (Hour 2 to 18), all systems including Comparative Example 1 (control) showed formation of tubular structures. According to observation at Hour 48 in the culture, Comparative Example 1 failed to maintain the tubular structures to cause their disruption. In Examples 1 to 4, the tubular structures were found to be maintained at Hour 72 in the culture. Since an angiogenic agent can be administered repeatedly, it is thought to be practically useful as a pharmaceutical in cases where it allows maintenance of the tubular structures for 72 hours in the culture.

Example 4 Stability Test

In order to test retention of the effect, and usefulness as a drug, each peptide was subjected to a stability test against endogenous cellular enzyme.

1. Method (1) Preparation of Protein Solution

Human vascular endothelial cells (HUVECs (Human Umbilical Vein Endothelial Cells, Promocell GmbH.)) were used. Cryopreserved HUVECs were cultured for 2 days in Endothelial Cell Growth Medium (Promocell GmbH.). The cells were detached and collected by a conventional method using trypsin-EDTA, and washed with $H_2O$, followed by addition of Lysis Buffer for Enzyme extraction (5 mL of TBS pH 7.5, 5 mL of Triton X100 (trade name), 40 mL of $H_2O$ with cOmplete mini, manufactured by Roche) thereto. The resulting mixture was left to stand on ice for 30 minutes to lyse the cells. The resulting cell lysate was centrifuged at 13,000 rpm at 4° C. for 3 min, and the supernatant was collected. The protein concentration was measured at A280 (Nano drop, Thermofischer scientific), and then adjusted to 2 mg/mL to prepare a protein solution for an assay.

(2) Assay

In each of PCR tubes, 50 μL of each of four kinds of AGP solutions (2 mg/mL)+20 μL of the cell lysate (2 mg/mL)+30 μL of $H_2O$ were mixed together, and the resulting mixtures were incubated at 37° C. in an incubator for 0, 1, 3, or 6 hours. Thereafter, each mixture was heated in a hot water bath at 90° C. for 5 minutes to inactivate enzyme, and then subjected to LC-MS analysis. The remaining peptide was quantified based on the area value of the peak detected with UV 210 nm in LC.

2. Results

Figure 6:
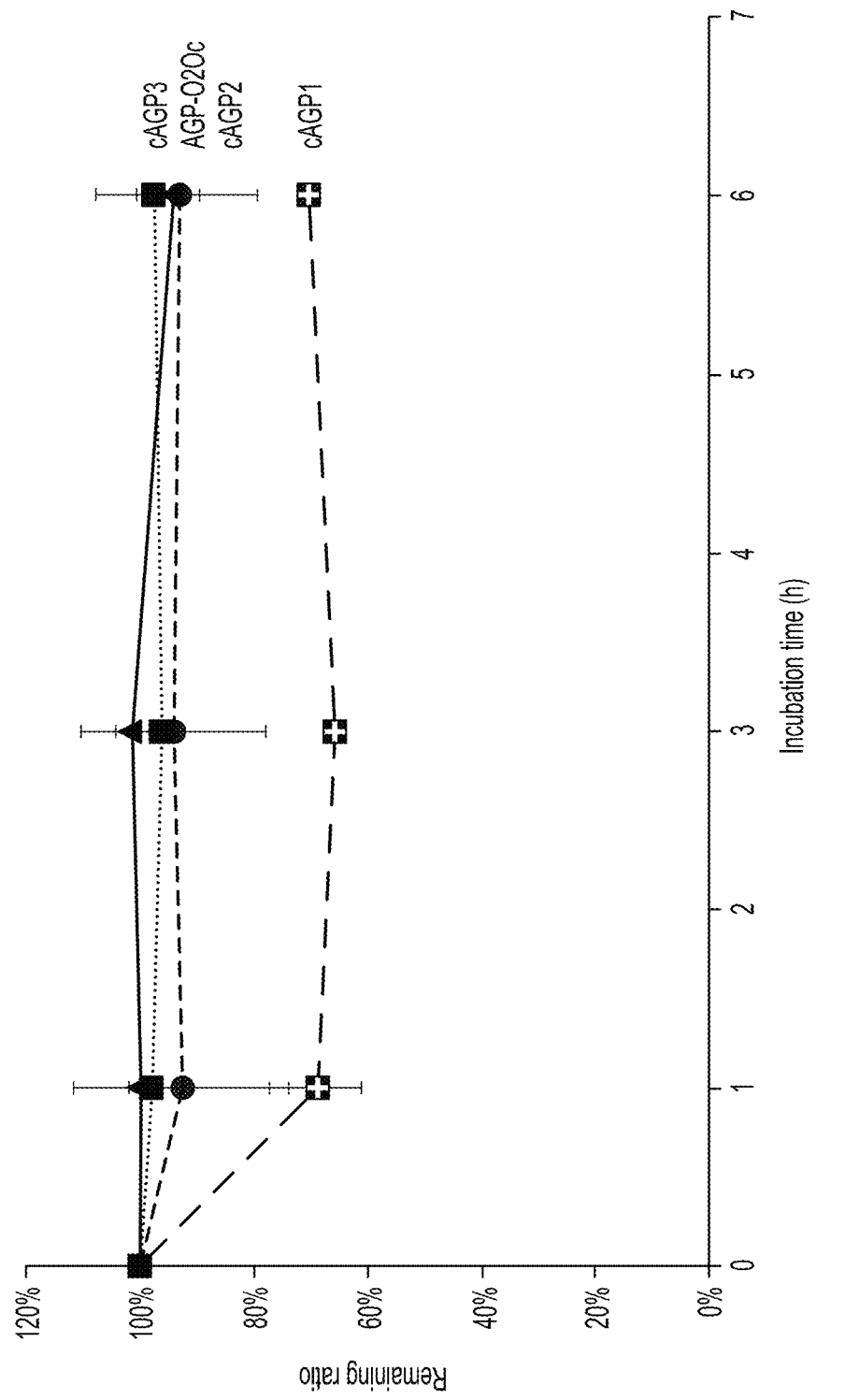
FIG. 6 is a diagram illustrating the results of the stability test for peptides, which test was carried out in the Examples below.

The results are shown in FIG. 6. As shown in FIG. 6, any of the compounds remained at not less than 70% at Hour 6. In particular, cAGP2 and cAGP3, each of which was formed by cyclization by linking of both ends of the peptide through a disulfide bond between Cys's, were found to have remained almost without degradation even after 6 hours of the assay. AGP-O2Oc also showed the same level of stability.

DESCRIPTION OF SYMBOLS

1 Well
2 Gel
3 Mixture of HUVEC cell suspension and each angiogenic factor

The invention claimed is:

1. A compound selected from formula [I]:

Cyclic(Cys-O₂Oc-SVV(F/Y)GLRG-Cys)-NH₂;

formula [II]:

Cyclic(O₂Oc-SVV(F/Y)GLRQ)-NH₂;

or formula [III]:

O₂Oc-SVV(F/Y)GLR-NH₂, wherein the number of oxyethylene units, represented by O₂Oc, is within the range of 2 to 6.

2. The compound according to claim 1, wherein the compound is of formula [IV]:

Cyclic(Cys-O₂Oc-SVVFGLRG-Cys)-NH₂, wherein the number of oxyethylene units, represented by O₂Oc, is within the range of 2 to 6.

3. The compound according to claim 2, wherein the compound is of formula [V]:

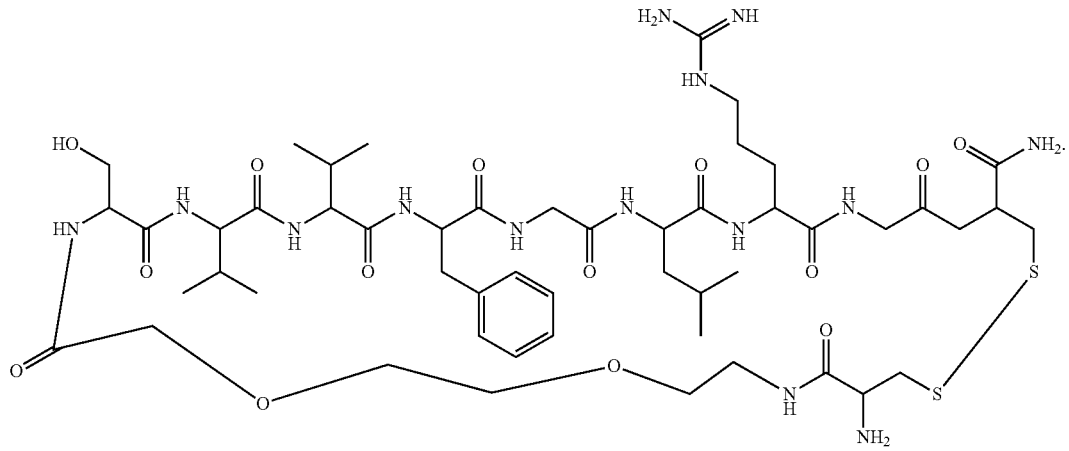 [SMILES: CC(C)CC1NC(=O)CNC(=O)C(Cc2ccccc2)NC(=O)C(C(C)C)NC(=O)C(C(C)C)NC(=O)C(CO)NC(=O)COCCOCCNC(=O)C(N)CSSCC(C(N)=O)CC(=O)CNC(=O)C(CCCNC(=N)N)NC1=O]

4. The compound according to claim 3, wherein the two cysteine residues in formula [V] are L-isomers.

5. The compound according to claim 3, wherein the two cysteine residues in formula [V] are D-isomers.

6. The compound according to claim 1, wherein the compound is of formula [VI]:

Cyclic(O₂Oc-SVVFGLRQ)-NH₂, wherein the number of oxyethylene units, represented by O₂Oc, is within the range of 2 to 6.

7. The compound according to claim 2, wherein the compound is of formula [VII]:

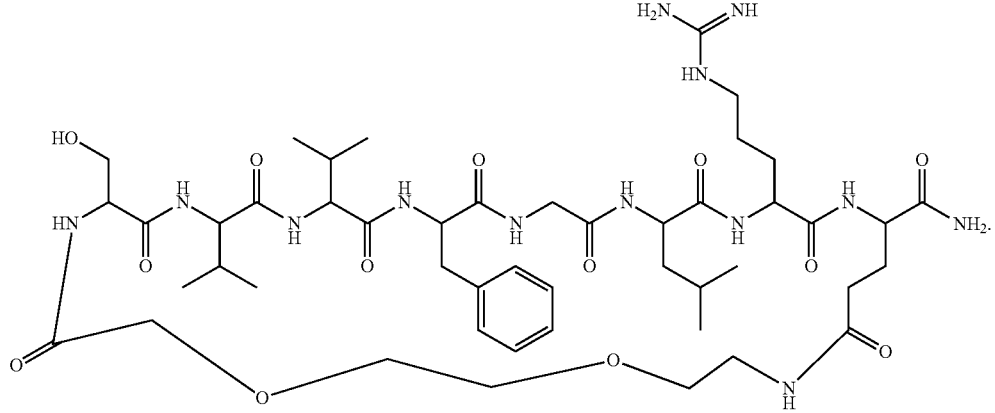 [SMILES: CC(C)CC1NC(=O)CNC(=O)C(Cc2ccccc2)NC(=O)C(C(C)C)NC(=O)C(C(C)C)NC(=O)C(CO)NC(=O)COCCOCCNC(=O)CCC(C(N)=O)NC(=O)C(CCCNC(=N)N)NC1=O]

8. The compound according to claim 1, wherein the compound is of formula [VIII]:

O₂Oc-SVVFGLR-NH₂, wherein the number of oxyethylene units, represented by O₂Oc, is within the range of 2 to 6.

9. The compound according to claim 8, wherein the compound is of formula [IX]:

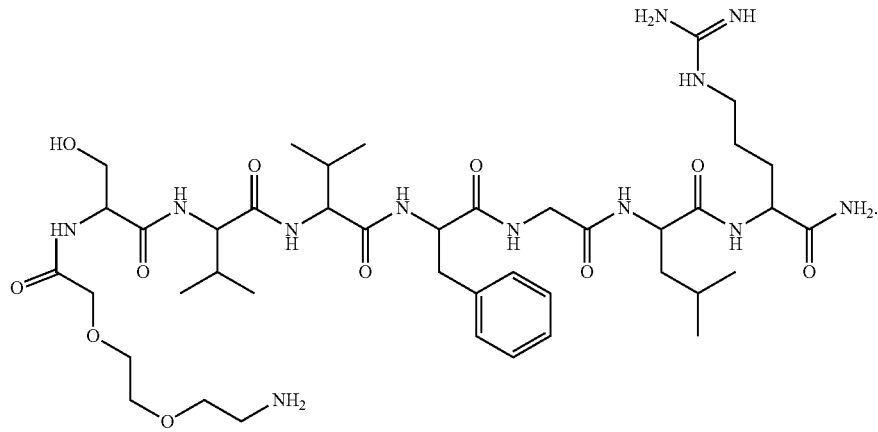 [SMILES: CC(C)CC(NC(=O)CNC(=O)C(Cc1ccccc1)NC(=O)C(NC(=O)C(NC(=O)C(CO)NC(=O)COCCOCCN)C(C)C)C(C)C)C(=O)NC(CCCNC(=N)N)C(N)=O]

10. An angiogenic agent comprising the compound according to claim 1 as an active component.

11. The angiogenic agent according to claim 10, wherein the compound is bound to a carrier.

12. A method comprising administering an effective amount of the compound according to claim 1 to a subject in need of angiogenesis.

\* \* \* \* \*

SEQUENCE LISTING

<160> NUMBER OF SEQ ID NOS: 6

<210> SEQ ID NO 1
<211> LENGTH: 8
<212> TYPE: PRT
<213> ORGANISM: artificial
<220> FEATURE:
<223> OTHER INFORMATION: angiogenic peptide

<400> SEQUENCE: 1

Ser Val Val Phe Gly Leu Arg Gly
1               5

<210> SEQ ID NO 2
<211> LENGTH: 8
<212> TYPE: PRT
<213> ORGANISM: artificial
<220> FEATURE:
<223> OTHER INFORMATION: angiogenic peptide

<400> SEQUENCE: 2

Ser Val Val Tyr Gly Leu Arg Gly
1               5

<210> SEQ ID NO 3
<211> LENGTH: 8
<212> TYPE: PRT
<213> ORGANISM: artificial
<220> FEATURE:
<223> OTHER INFORMATION: angiogenic peptide

<400> SEQUENCE: 3

Ser Val Val Phe Gly Leu Arg Gln
1               5

<210> SEQ ID NO 4
<211> LENGTH: 8
<212> TYPE: PRT
<213> ORGANISM: artificial
<220> FEATURE:
<223> OTHER INFORMATION: angiogenic peptide

<400> SEQUENCE: 4

Ser Val Val Tyr Gly Leu Arg Gln
1               5

<210> SEQ ID NO 5
<211> LENGTH: 7
<212> TYPE: PRT
<213> ORGANISM: artificial
<220> FEATURE:
<223> OTHER INFORMATION: angiogenic peptide

<400> SEQUENCE: 5

Ser Val Val Phe Gly Leu Arg
1               5

<210> SEQ ID NO 6
<211> LENGTH: 7
<212> TYPE: PRT
<213> ORGANISM: artificial
<220> FEATURE:
<223> OTHER INFORMATION: angiogenic peptide

```
<400> SEQUENCE: 6

Ser Val Val Tyr Gly Leu Arg
1               5
```